United States Patent
Grodzki et al.

(10) Patent No.: US 11,619,695 B2
(45) Date of Patent: Apr. 4, 2023

(54) METHOD AND DEVICE FOR MAGNETIC RESONANCE IMAGING, AND CORRESPONDING COMPUTER PROGRAM PRODUCT

(71) Applicant: Siemens Healthcare GmbH, Erlangen (DE)

(72) Inventors: David Grodzki, Erlangen (DE); Gregor Koerzdoerfer, Erlangen (DE); Mathias Nittka, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 182 days.

(21) Appl. No.: 17/139,304

(22) Filed: Dec. 31, 2020

(65) Prior Publication Data
US 2021/0208228 A1    Jul. 8, 2021

(30) Foreign Application Priority Data
Jan. 3, 2020 (EP) .................................... 20150158

(51) Int. Cl.
| | | |
|---|---|---|
| *G01R 33/56* | (2006.01) | |
| *G01R 33/44* | (2006.01) | |
| *G01R 33/483* | (2006.01) | |
| *G01R 33/50* | (2006.01) | |
| *G01R 33/561* | (2006.01) | |

(Continued)

(52) U.S. Cl.
CPC ....... *G01R 33/5608* (2013.01); *G01R 33/445* (2013.01); *G01R 33/4833* (2013.01); *G01R 33/50* (2013.01); *G01R 33/5614* (2013.01); *G01R 33/58* (2013.01); *A61B 5/055* (2013.01)

(58) Field of Classification Search
None
See application file for complete search history.

(56) References Cited

U.S. PATENT DOCUMENTS

| | | | | |
|---|---|---|---|---|
| 10,162,031 | B2 * | 12/2018 | Tunnicliffe | ........... A61B 5/055 |
| 2004/0204644 | A1 * | 10/2004 | Tsougarakis | ............ B23P 19/00 |
| | | | | 324/309 |

(Continued)

FOREIGN PATENT DOCUMENTS

EP    3572824 A1    11/2019

OTHER PUBLICATIONS

R. Treier, A. Steingoetter, M. Fried, W. Schwizer, P. Bösiger: "Fast T1 mapping for the assessment of intragastric distribution, dilution and mixing", International Society for Magnetic Resonance in Medicine, No. 427, 427, Jan. 1, 2005 (Jan. 1, 2005), XP040593111.

(Continued)

*Primary Examiner* — Rodney E Fuller
(74) *Attorney, Agent, or Firm* — Banner & Witcoff Ltd.

(57) ABSTRACT

In a Method and a device for magnetic resonance imaging of a subject using a spoiled gradient echo sequence, a $B_0$ magnetic field strength of at most 1.5 T is used during the sequence. As part of the sequence a slice select gradient acting as a spoil gradient is played out. Substantially simultaneously with the slice select gradient a predetermined RF pulse is played out in the sequence, wherein a time-bandwidth product of the RF pulse is set so that a majority of the energy of the RF pulse is transmitted in its central main lobe.

18 Claims, 1 Drawing Sheet

(51) Int. Cl.
*G01R 33/58* (2006.01)
*A61B 5/055* (2006.01)

(56) References Cited

U.S. PATENT DOCUMENTS

2006/0061358 A1  3/2006  Hargreaves et al.
2019/0361086 A1  11/2019 Nittka et al.

OTHER PUBLICATIONS

Gregor Körzdörfer et al: "Magnetic resonance field fingerprinting", Magnetic Resonance in Medicine., Oct. 15, 2018 (Oct. 15, 2018), XP055516998, US ISSN: 0740-3194, DOI: 10.1002/mrm.27558.
Dan Ma et al: "Magnetic resonance fingerprinting"; Nature, vol. 495, No. 7440, pp. 187-192, XP055183037, ISSN: 0028-0836, DOI: 10.1038/nature11971; 2013.
Jiang, Yun et al., "MR Fingerprinting Using Fast Imaging with Steady State Precession (FISP) with Spiral Readout", Magnetic Resonance in Medicine, vol. 74, pp. 1621-1631, 2015 // DOI: 10.1002/mrm.25559.
European Search Report dated Jul. 13, 2020, Application No. 20150158.2.

\* cited by examiner

METHOD AND DEVICE FOR MAGNETIC RESONANCE IMAGING, AND CORRESPONDING COMPUTER PROGRAM PRODUCT

CROSS REFERENCE TO RELATED APPLICATIONS

This patent application claims priority to European Patent Application No. 20150158.2, filed Jan. 3, 2020, which is incorporated herein by reference in its entirety.

BACKGROUND

Field

The present disclosure relates to a method for magnetic resonance imaging of a subject as well as to a corresponding device for magnetic resonance imaging. The present disclosure further corresponds to a computer program product comprising instructions for executing said method.

Related Art

Magnetic resonance imaging (MR imaging, MRI) is by now a well-known and well-established imaging and examination technique which is mainly used in the medical field but can also have other industrial applications. While it is known that in principle quantitative magnetic resonance imaging is possible and can be used to measure absolute properties of a respective subject, conventional MR sequences used in the current clinical routine typically only measure a relative signal intensity for different types of tissue. Using such relative or qualitative MR imaging means that a diagnostic interpretation of resulting MR images can be highly dependent on a subjective assessment or evaluation by a respective radiologist or other medical personnel.

Quantitative MR imaging techniques would as a main advantage provide an improved objective comparability resulting in a potentially more reliable and reproducible diagnosis. However, quantitative MR imaging techniques are rarely used, because they have a major disadvantage in typically being more complex and requiring significantly longer measurement periods that are impractical for the clinical routine. It has also been observed that proposed techniques for quantitative MR imaging can show unwanted influences because of $B_0$ offsets and $B_0$-inhomogeneities, heightened diffusion sensitivity, et cetera.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
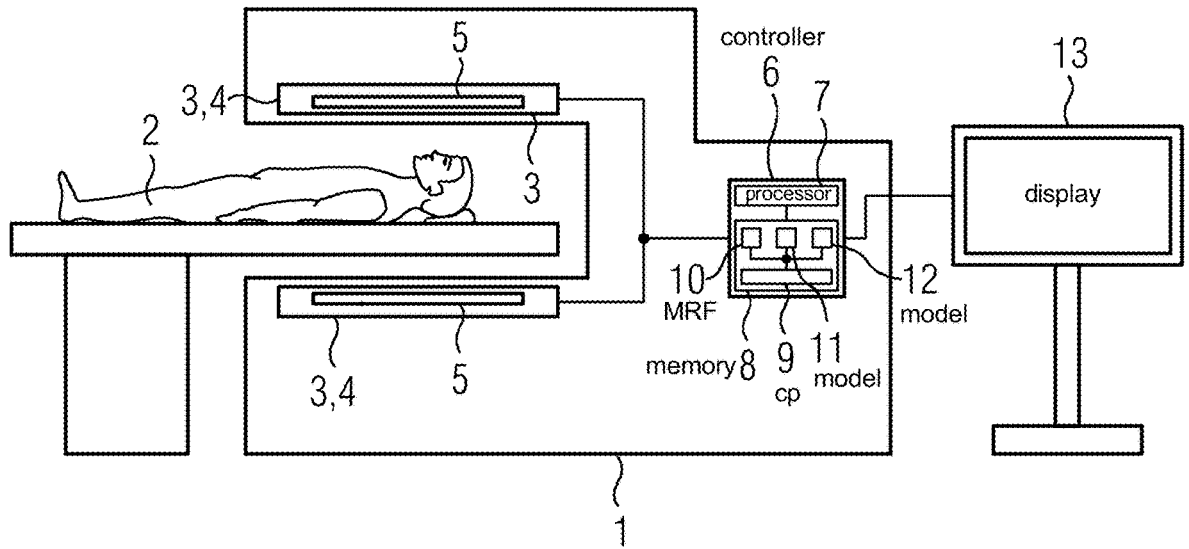
FIG. 1 shows a magnetic resonance imaging device configured for quantitative MR imaging of a subject according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

It is an objective of the present disclosure to reduce a $B_0$ sensitivity in MR imaging with particularly low effort.

A method according to the present disclosure is adapted and thus usable for magnetic resonance imaging of a subject. The subject can, for example, be a patient, a part of a patient, or any other object that is suitable for MR imaging. The method according to the present disclosure uses or employs a spoiled gradient echo sequence. In the method according to the present disclosure a $B_0$ magnetic field strength of at most 1.5 T is used. In other words, the method uses or is a low field MRI technique. As is common in the field of MR imaging, $B_0$ refers to a main static magnetic field.

In a process step of the method according to the present disclosure as part of the sequence a slice select gradient acting as a spoil gradient is played out. In another step of the method substantially simultaneously with the slice select gradient a predetermined RF pulse (RF: radiofrequency) is played out in the sequence. Therein, a time-bandwidth product (TBP) of the RF pulse is set so that a majority of the energy of the RF pulse is transmitted in its central main lobe. This means that at least 50%, preferably at least 75% or even at least 85%, of the total power or energy of the RF pulse is contained in the main lobe, while parts of the respective RF pulse before and after the main lobe contain correspondingly less power or energy. To achieve this, a conventional MR sequence with substantially Gaussian or sinusoidal RF pulses can be used as a starting point from which the TBP of the RF pulse is increased until the above-mentioned condition is met. Typical conventional sequences may use RF pulses with TBPs of about 2-3 or even less resulting in a substantially Gaussian, sinusoidal or rectangular signal form of the RF pulse.

The method according to the present disclosure is particularly suitable for quantitative MR imaging and can advantageously offer reduced $B_0$ sensitivity as well as reduced complexity and required time when compared to known conventional quantitative MR imaging techniques. For example, proposed techniques for so-called magnetic resonance fingerprinting (MRF) are based on the ideas that because of unbalanced gradient moments within each repetition time interval TR the magnetisation is completely dephased before it is flipped by each RF pulse, and that the dephasing moment imparted by an unbalanced slice select gradient is sufficient so that a $B_0$-dependency of a measured MR signal can be completely disregarded.

The present disclosure is based on the insight that both of these assumptions cannot be considered to be true under all circumstances. Rather, it has been shown that in a slice-selective 2D magnetic resonance fingerprinting implementation with traditional or conventional gradient and RF pulse signal forms the magnetisation is in fact not always completely dephased before the RF pulse is played out and starts to apply the flip angle. With slice-selective RF pulses $B_1^+$ and thus the flip angle is typically applied while the spins are still being dephased when the slice select gradient just begins. Therefore, one cannot assume that the magnetisation or the spins are already completely dephased before they are flipped.

These problems are solved in the present disclosure by using an RF pulse or RF pulses with a relatively high TBP. With the increased, relatively high TBP a first part of the RF pulse before the main lobe can in fact be neglected, since it does not contain enough power and energy to cause the spins to flip. This means that the spoil gradient has more time to effectively dephase the magnetisation or the spins before the main lobe of the RF pulse hits, so that at that point the dephasing is actually substantially complete. This effectively eliminates or significantly reduces the $B_0$ sensitivity of the resulting measured MR signal. It also enables as a significant advantage of the present disclosure that the slice select gradient itself can be used as a spoil gradient to dephase the spins, meaning that an additional or separate dephasing gradient or dephasing moment is not needed and can be forgone entirely or at least significantly reduced or shortened. This can significantly decrease a complexity and required time for imaging the respective subject using the method according to the present disclosure when compared to conventional techniques.

It is another insight of the present disclosure that RF pulses with relatively high TBPs, i.e. for example TBPs of at least 5, can be practically used in combination with low field MRI, i.e. with $B_0$ field strength of at most 1.5 T. This is the case, because at these lower $B_0$ field strengths there is a correspondingly lower SAR (specific absorption rate) which offers the flexibility to actually use higher TBPs without exceeding a given SAR threshold as might typically be the case at higher $B_0$ field strengths.

An actual value for the TBP for the at least one RF pulse or any or all RF pulses of the sequence can be predetermined as an input or a parameter or parameter value. It may be set to a fixed value for use in the method according to the present disclosure. It can, however, be set or adapted for each application or use case individually, for example depending on characteristics or limitations of a respective used magnetic resonance imaging device, a respective actual $B_0$ field strength, a strength of the slice select gradient, whether or not an additional spoil gradient is used, characteristics of the respective subject, a given SAR threshold, and/or the like.

While a higher TBP can be advantageous and preferable in terms of resulting image quality and consistency, a lower TBP might be used to take into account one or more of the above-mentioned factors. While a lower TBP might result in more unwanted off-resonance effects, the method according to the present disclosure can still offer advantages over conventional methods and sequences with even lower TBPs. Some specific values will be discussed in further detail down below.

In an advantageous development of the present disclosure a predetermined threshold value is provided and the TBP is set so that the threshold value is met. The threshold value can preferably be or refer to a $B_0$-dependency of the measured MR signal, a spin dephasing at the time of the main lobe of the RF pulse, and/or off-resonance effects. To meet the threshold value the TBP can, for example, be increased stepwise from a given, i.e. predetermined, starting value. The starting value can, for example, be a standard value typically used in conventional MR sequences today, for example in the range of 2-3 or less. Setting the TBP depending on the predetermined threshold value as described herein can offer an advantageous flexibility for using the method according to the present disclosure in different situations, different circumstances, and/or for different applications. It can also offer an advantageously simple and easy way for a respective user to adapt the method to specific individual needs or requirements, because the user can simply just set the threshold value as a predetermined value or input parameter, whereafter the TBP to be used can then be determined and set automatically as described below. By increasing the TBP from the given starting value, a minimum TBP that meets or fulfils the threshold value or corresponding conditions or requirements these can advantageously be met while at the same time advantageously limiting the exposure of the subject and/or the strain on the respective magnetic resonance imaging device.

In a further advantageous development of the present disclosure the value to be used for the TBP is determined experimentally by imaging a phantom object multiple times with different settings and analysing respective results in comparison with the predetermined threshold value. In other words, a database or table can be provided that is filled with corresponding experimentally determined values for the threshold characteristics with the corresponding TBP. The TBP to be used can then be determined from this database or table by looking up the predetermined threshold value. This can be done either manually or automatically or semi-automatically. Advantageously, the experimental determination has to be done only once, after which the database or table offers a particularly easy, fast, and simple to use method for determining the required TBP for a given threshold value.

In a further advantageous development of the present disclosure the value to be used for the TBP is determined based on modelling or simulating the imaging process or part thereof using a predetermined model or simulation. This can in particular be used to model or simulate a spin dephasing or evolution due to the spoil gradient, i.e. the slice select gradient and, if applicable, any additional dephasing gradients or moments, preferably in conjunction with a signal form or time evolution of the RF pulse, in particular its effect on flipping the spins. This approach can advantageously be combined with the described predetermined threshold value. This means, that the imaging process or part thereof can be modelled or simulated for different TBPs or in dependence on the TBP to determine the required value to meet the predetermined threshold value. The modelling or simulation can be performed for each subject or application individually, which offers the advantageous possibility to adapt the model or simulation correspondingly. For example, characteristics or parameters of the respective magnetic resonance imaging device and/or the respective subject can be input into the model or simulation as predetermined parameters. It is, however, also possible to perform the modelling or simulation in advance, i.e. before the actual imaging of the subject. This can for example be done for a mean or standard situation or for multiple different magnetic resonance imaging devices and/or objects of subject characteristics. Performing the modelling or simulation in advance can offer the advantage of being able to employ greater complexity, precision and computing time, and can also minimise any delays during the actual imaging of the respective subject.

In a further advantageous development of the present disclosure the imaging process is modelled or simulated in dependence on a voxel size and/or a flip angle predetermined for the respective imaging process, i.e. for the MR sequence, an MR protocol, or the like. For example, bigger voxel sizes can mean a correspondingly reduced dephasing moment. A dependency on the flip angle may, however, not necessarily be so simple so that it is not immediately clear or obvious, which combination of higher or lower TBP and higher or lower flip angle will produce optimal results, for example in terms of $B_0$ sensitivity, diffusion sensitivity, off-resonance effects, and/or the like. Here, the modelling or simulation can therefore advantageously lead to further improved imaging results.

In a further advantageous development of the present disclosure the TBP is set to a maximum value that still observes a predetermined SAR value and/or that observes a predetermined hardware limitation of the respective magnetic resonance imaging device used for carrying out the method. Such a hardware limitation can, for example, be a maximum voltage, a maximum transmitting power of a radiofrequency power amplifier (RFPA), an achievable peak magnetic field strength or gradient, and/or the like. Not exceeding these limitations or the allowed SAR value or threshold is obviously advantageous. Maximising the TBP within these limitations or boundaries—for example in contrast to setting the TBP to a minimum functional or workable value—can advantageously further reduce unwanted $B_0$ sensitivity or $B_0$ influences and/or off-resonance effects in the respective measured MR signal and can therefore lead to improved image quality and/or consistency. As described, the maximum value for the TBP can be determined experimentally and/or through modelling or simulating at least part of the imaging process.

In a further advantageous development of the present disclosure the TBP is set to a value of at least 6, preferably to a value of at least 8. It has been found that at these TBP values the spins can be substantially completely dephased at the time the central main lobe of the RF pulse hits so that the described benefits of the method according to the present disclosure can be reliably achieved.

In a further advantageous development of the present disclosure a FISP-sequence (fast imaging with steady-state precession) is used for imaging the subject. A FISP-sequence is a steady-state coherent gradient echo sequence, typically with refocusing of the FID (free induction decay). In contrast to TrueFISP and other balanced sequences, it has been found that FISP-sequences can be significantly less sensitive to variations of or in the static magnetic field $B_0$, which works very well for the proposed method according to the present disclosure and supports or further facilitates its advantages. Compared to a basic gradient echo sequence, a FISP sequence can, for example, comprise phase-alternating RF pulses, constant extra gradients in the readout and/or slice-selecting directions, and/or variable rewinder gradients along the phase-encoding axis as additional modifications.

In a further advantageous development of the present disclosure as part of the FISP-sequence an adiabatic 180° inversion pulse is followed by application of a predetermined pseudo random flip angle series, and each resulting echo is read out using a spiral k-space sampling pattern. Therein, the inversion pulse causes a targeted disturbance of the equilibrium state. It has been found, that in this manner typically very advantageous results can be achieved with the method according to the present disclosure.

In a further advantageous development of the present disclosure for imaging the subject a magnetic resonance fingerprinting method is used. This MR fingerprinting method or process comprises simulating a plurality of MR signals for different combinations of various T1- and T2-relaxation times, and matching a measured MR signal to the simulated MR signals to determine the T1- and T2-relaxation times for the respective subject. The collection of different simulated MR signals do, in other words, function as a dictionary or reference to which the respective MR signal that is actually measured from the respective subject is compared. The simulated MR signal that best matches, i.e. is closest or most similar to the measured MR signal is determined and selected, and the T1- and T2 relaxation times that were used as a basis for this selected simulated MR signal are then taken to be or describe the actual T1- and T2-relaxation times for the respective subject.

Advantageously, the simulation can be limited to the actual spin physics for T1- and T2-relaxation times, thereby limiting a necessary computational effort and making it feasible to simulate a relatively large number, for example at least several hundred or several thousand, combinations of T1- and T2-relaxation times, for example over time ranges of 1 ms to 2000 ms. Using this magnetic resonance fingerprinting method can advantageously reduce the required measurement time to the point where quantitative MR imaging becomes practical even for the clinical routine. It thus offers a relatively easy and straightforward to implement way of realising the method according to the present disclosure and its described advantages and benefits in more applications or scenarios and with improved reliability and consistency compared to conventional quantitative MR imaging techniques and currently used relative or qualitative MR imaging techniques, respectively.

Advantageously, the simulation of the plurality of MR signals can be done in advance and the results can be stored in a database or table. This advantageously limits the amount of computational resources and the imaging time needed at the acquisition time of MR data for of the respective subject. It also means that the simulation can be done using more time and computational resources and thus more precision than is typically feasible in the clinical routine.

In a further advantageous development of the present disclosure to determine the measured MR signal a sequence of multiple RF pulses, i.e. a predetermined number of RF pulses, are played out. Each of these multiple RF pulses has the set, relatively high TBP. These multiple RF pulses result in a corresponding number of echoes or echo trains that are read out, wherein each readout provides a data point, and the measured MR signal consists of the corresponding sequence of all these data points. The measured MR signal or its form or waveform or evolution is, in other words, extracted from a serious of n individual images, where n is the predetermined number of the multiple RF pulses. The measured MR signal is, in other words, determined or tracked over multiple RF pulses and thus multiple TR intervals and represents or describes the development, change, or evolution of the relaxation times of the respective subject during the imaging process. This offers a simple, easy, and fast way to determine the measured MR signal, since only a series of individual images needs to be processed or analysed.

In a further advantageous development of the present disclosure from each of the echoes or echo trains a single image is reconstructed and the measured MR signal is extracted from the resulting series of single images per pixel. In other words, a separate individual measured MR signal is determined or extracted for each pixel stack or pixel coordinate or position of the stack or series of individual images. This means, that a single measured MR signal spans the whole series of individual images but only at a single pixel coordinate or position. Therefore, each measured MR signal tracks or describes the evolution at an individual pixel coordinate or position. This advantageously provides a per-pixel resolution and accuracy and can thus lead to particularly accurate and reliable results.

In a further advantageous development of the present disclosure the slice selection gradient is the only spoil gradient used in the MR sequence for imaging the subject. In other words, no additional or separate dephasing gradient or spoil gradient or moment other than the slice select gradient is applied. This development of the present disclosure is based on the insight that the slice selection gradient is typically strong enough to achieve substantially complete dephasing of the spins in the time before the main lobe of the respective RF pulse is played out or applied. By foregoing a separate or additional spoil gradient the sequence can advantageously be shortened, thereby making the method according to the present disclosure practical for routine clinical applications, and reducing strain for the respective subject.

Another aspect of the present disclosure is a magnetic resonance imaging device. This magnetic resonance imaging device is equipped with an electromagnetic subsystem adapted for imaging a subject, and comprises means adapted and configured to execute or carry out at least one development or variant of the method according to the present disclosure. In particular, the magnetic resonance imaging device according to the present disclosure can be the magnetic resonance imaging device mentioned in conjunction with the method according to the present disclosure and can therefore be adapted and configured correspondingly as described in connection with the method according to the present disclosure. The electromagnetic subsystem can comprise typical well-known components for magnetic resonance imaging, such as magnets or coils, an RF pulse generator, a corresponding power amplifier, a controller, and the like. The means for carrying out the method according to the present disclosure can in particular comprise a data processing means, which, for example, can be part of or integrated into the controller of the magnetic resonance imaging device. The data processing means can in particular comprise a processor, a microchip, a controller, an integrated circuit, and/or the like, as well as a data store connected thereto. The data processing means can be adapted and configured to execute a computer program or program code stored on or in data store to carry out the method according to the present disclosure. This computer program or program code can thus implement or encode the instructions or process steps of the method according to the present disclosure, for example as methods, functions, program modules, and/or the like.

Another aspect of the present disclosure is a computer program product comprising instructions that, when executed cause the magnetic resonance imaging device according to the present disclosure to carry out at least one development or variant of the method according to the present disclosure. The computer program product according to the present disclosure can be a computer program or program code implementing or encoding the method according to the present disclosure, i.e. its processes process steps.

The computer program product according to the present disclosure can also be or comprise a computer-readable storage medium having stored thereon such a computer program or program code.

In particular, the magnetic resonance imaging device according to the present disclosure can comprise at least one computer program product according to the present disclosure, for example in the form of the mentioned data store and/or the computer program or program code stored thereon.

The embodiments and developments of the present disclosure described herein for at least one aspect of the present disclosure, that is, at least for the method, the magnetic resonance imaging device, and the computer program product as well as the corresponding advantages may be applied to any and all aspects of the present disclosure.

The examples described below refer to exemplary embodiments of the present disclosure. Therein, individual components and process steps of the embodiments each constitute individual, independent features of the present disclosure that can further develop the disclosure independently of each other as well as in combinations not explicitly described. The described embodiments can be further developed or supplemented by features, components and/or steps already described above.

FIG. 1 schematically shows a magnetic resonance imaging device—or MRI device 1 for short—that can be used for quantitative imaging of a subject, such as presently a patient 2 placed therein. The MRI device 1 comprises a subsystem 3 for acquiring MR signals of or from the patient 3. The subsystem 3 is illustrated here only schematically and comprises at least a main coil 4 for generating a static magnetic field $B_0$, and a gradient coil 5 for generating a magnetic gradient field, such as a slice select gradient. The subsystem 3 is also adapted to generate RF pulses to apply a predetermined flip angle to spins in the patient 2. The subsystem 3 can also comprise additional components or parts as is standard for magnetic resonance imaging apparatuses and/or as needed for more complex MR measurements, such as additional coils, magnets, electric or electronic parts, shielding, and the like.

The MRI device 1 further comprises a data processing and controller 6 that is connected to the subsystem 3. The controller 6 is adapted to control the MRI device 1 to acquire MRI data, and to process this data to generate an MR image of at least part of the patient 2. For these purposes the controller 6 presently schematically comprises a processor 7 and connected thereto a data store 8. The data store 8 can be a single unit or comprise multiple parts, such as a permanent mass storage device and/or a transient memory device. The data store 8 can, for example, be or comprise a hard disk drive, a solid-state disk, a flash drive, random access memory, and/or the like.

Presently, in the data store 8 there is stored a computer program 9 that is adapted and configured to be executed by the processor 7 and that comprises instructions to cause the controller 6 or the MRI device 1 to execute a method for imaging the patient 2 as described herein. Additionally, the data store 8 presently contains an MRF dictionary 10, which is a database of simulated MR signals and corresponding T1- and T2-relaxation times on which the simulated MR signals are based. Also stored in the data store 8 are a first computer model 11 for simulating the MR signals and a second computer model 12 for determining a suitable time-bandwidth product (TBP) for RF pulses used in imaging the patient 2.

Any output or data, such as an MR image of the patient 2, generated by the controller 6 or the MRI device 1 in general can be output to a display device 13 connected thereto and/or to another data processing device.

Figure 2:
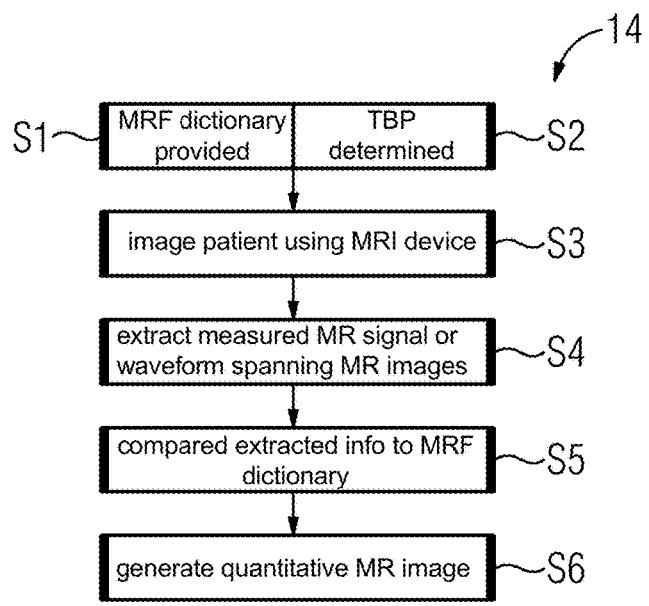
FIG. 2 is a flowchart of a method for quantitative MR imaging of the subject according to an exemplary embodiment.

FIG. 2 schematically illustrates an exemplary flow chart 14 with process steps S1 to S6 detailing a method for quantitative MR imaging of a subject, such as the patient 2 using the MRI device 1.

In process step S1 the MRF dictionary 10 is either provided as a predetermined input or is generated by the controller 6 or an external data processing device by using the first computer model 11 to simulate measured MR signals for multiple different combinations of various T1- and T2-relaxation times. This is part of a magnetic resonance fingerprinting method (MRF method) presently used for imaging the patient 2.

In process step S2 the TBP for the RF pulses used in imaging the patient 2 is determined. This can be done manually, for example by a user setting the TBP as a predetermined input. Preferably, the TBP is determined automatically or semi-automatically by the controller 6 using the second computer model 12. Here, one or more predetermined conditions or threshold values that are to be met by the TBP and/or by or during the imaging process can be provided as a basis or input or as parameters for the second computer model 12. As part of the presently described method the TBP is advantageously determined and set in a controlled manner, for example instead of either using the standard relatively low TBP of conventional imaging techniques resulting in substantially rectangular RF pulses or just maximising the TBP within the hardware limits of the MRI device 1 resulting in—potentially unnecessary—increased SAR strain for the patient 2.

The process steps S1 and S2 can be performed in parallel as indicated in the flowchart 14 or they can be performed one after the other. Both the process steps S1 and S2 can preferably be performed before actually applying any magnetic fields to the patient 2 as part of the actual imaging process to allow for a faster, more efficient imaging process without any pauses or delays between acquiring MR data, i.e. measuring the MR signals of the patient 2 and reconstructing or outputting corresponding MR images.

Presently, the TBP for one, multiple or all RF pulses used in a sequence for imaging the patient 2 is set to at least 6 are at least 8.

Using this sequence and a predetermined $B_0$ field strength of at most 1.5 T in process step S3 the patient 2 is imaged using the MRI device 1, meaning that measured MR signals of or for the patient 2 are acquired. In particular, a sequence or implementation for 2D MRF is used. Therein, a slice select gradient, which is played out substantially simultaneously with each of the RF pulses, is used as a spoil gradient, and in particular as the only spoil gradient of the sequence. Due to the relatively high TBP of the RF pulses the slice select gradient can achieve a substantially complete dephasing of the spins before a respective main lobe of the RF pulses is played out or applied and causes the spins to flip by a predetermined flip angle.

Generally, any echo technique and any k-space sampling pattern can be used here, such as a Cartesian, spiral, or radial sampling pattern.

For a particularly robust and at the same time relatively easy method, presently a FISP-sequence in combination with a spiral k-space sampling pattern is used. Each of the predetermined number of n RF pulses generates a corresponding echo which is read out using a respective individual spiral sampling pattern. Based thereon, a series of n individual MR images is generated by the controller 6.

In process step S4 a measured MR signal or waveform spanning the serious of n individual MR images is extracted therefrom by the controller 6 for each pixel position or pixel coordinate, i.e. from each pixel stack.

In process step S5 these measured MR signals or waveforms are compared to the MRF dictionary 10 by the controller 6. Therein, for each measured MR signal or waveform the respective simulated MR signal that best matches it is determined. The corresponding T1- and T2-relaxation times for the respective best matching or best fitting simulated MR signal are then read out from the MRF dictionary 10 and used as the actual T1- and T2-relaxation times for the patient 2.

Based on these T1- and T2-relaxation times in process step S6 a respective quantitative MR image for the patient 2 is generated by the controller 6 and is output to the display device 13.

The flowchart 14 or its process steps S1 to S6 can represent functions or program modules of the computer program 9.

Overall, the described method can be used for magnetic resonance imaging, in particular quantitative magnetic resonance imaging based on MRF, with no or reduced $B_0$-dependency without requiring additional dephasing moments or gradients. By using low field MRI ($B_0 < 1.5$ T) the corresponding lower SAR can be capitalised upon to use RF pulses with increased TBP. With the increased TBP a correspondingly large part of a respective total RF power or energy of each RF pulse, for example at least 50% or at least 75% for at least 85%, is played out in a middle or central part of the respective RF pulse. Before and after this middle part the power of each RF pulse is correspondingly low enough so that it does not cause the spins to flip, i.e. does not apply the flip angle and can thus be disregarded. This means that during this first part before the central lobe of each RF pulse the spins are not yet flipped but are being completely dephased by the slice select gradient. Essentially, the TBP for each RF pulse is chosen or set so that a sufficient intrinsic dephasing is accomplished before the spins are flipped. For determining the respective sufficient TBP, it can be calculated, modelled or simulated using different methods or criteria, or experimental measurements or a test serious can be used. When determining or setting the TBP a given predetermined SAR threshold and/or system or device parameters, limitation, or characteristics, for example of the MRI device 1, can be used as a limit or as boundary conditions for maximising the TBP to completely utilise the available flexibility, i.e. space or margin, for example in terms of SAR or transmitting power, or the like. The presently described method can, in other words, be used to minimise a $B_0$ sensitivity of FISP-MRF through the use of our RF pulses with sufficiently high TBP.

The main advantages of the presently described method lie in MRF results essentially free of influences of $B_0$ offsets or inhomogeneities, in the non-necessity of additional dephasing gradients in addition to the slice select gradient, and in reduced diffusion sensitivity as well as shortened TRs and total required measurement times.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for magnetic resonance imaging of a subject using a spoiled gradient echo sequence, the method comprising:
    using a $B_0$ magnetic field strength of at most 1.5 T during the spoiled gradient echo sequence;
    providing a predetermined threshold value;
    applying, as part of the spoiled gradient echo sequence, a slice select gradient acting as a spoil gradient; and
    applying a predetermined radio frequency (RF) pulse in the spoiled gradient echo sequence simultaneously with the slice select gradient, wherein a time-bandwidth product (TBP) of the RF pulse is set so that: a majority of an energy of the RF pulse is transmitted in its central main lobe, and the threshold value is met through a stepwise increase from a given starting value.

2. The method according to claim 1, wherein the predetermined threshold value is for a $B_0$-dependency of a measured magnetic resonance (MR) signal, for a spin dephasing at the time of the main lobe, and/or for off-resonance effects.

3. The method according to claim 1, wherein a value to be used for the TBP is determined experimentally by imaging a phantom object multiple times with different settings and analyzing respective results in comparison with the predetermined threshold value.

4. The method according to claim 1, wherein a value to be used for the TBP is determined based on modelling or simulating an imaging process including a spin dephasing due to the spoil gradient using a predetermined model or simulation.

5. The method according to claim 4, wherein the imaging process is modelled or simulated based on a voxel size and/or on a flip angle predetermined for the respective imaging process.

6. The method according to claim 1, wherein the TBP is set to a maximum value that observes a predetermined specific absorption rate (SAR) value and/or a predetermined hardware limitation of a respective magnetic resonance imaging device.

7. The method according to claim 1, wherein the TBP is set to a value of at least 6.

8. The method according to claim 1, wherein a fast imaging with steady-state precession sequence (FISP-sequence) is used for imaging the subject.

9. The method according to claim 8, wherein the FISP-sequence comprises an adiabatic 180° inversion pulse followed by application of a pseudorandom flip angle series, each resulting echo being read out using a spiral k-space sampling pattern.

10. The method according to claim 1, wherein, to image the subject, a magnetic resonance fingerprinting method is used that comprises:
   simulating a plurality of magnetic resonance (MR)-signals for different combinations of various T1- and T2-relaxation times, and
   matching a measured MR-signal to the plurality of simulated MR-signals to determine the T1- and T2-relaxation times for the subject.

11. The method according to claim 10, further comprising: to determine the measured MR-signal, applying a sequence of multiple RF-pulses resulting in a corresponding number of echoes or echo trains that are read out, wherein each readout provides a data point, and the measured MR-signal includes the sequence of all corresponding data points.

12. The method according to claim 11, further comprising, from each of the echoes or echo trains, reconstructing a single image and extracting the measured MR-signal from the resulting series of single images per pixel.

13. The method according to claim 1, wherein the slice selection gradient is the only spoil gradient used in the sequence for imaging the subject.

14. A computer program product, embodied on a non-transitory computer-readable storage medium, including a program and being directly loadable into a memory of a magnetic resonance imaging device, when executed by a processor of the magnetic resonance imaging device, causes the processor to perform the method as claimed in claim 1.

15. A non-transitory computer-readable storage medium with an executable program stored thereon, that when executed, instructs a processor to perform the method of claim 1.

16. The method according to claim 1, wherein the predetermined threshold value is based on a $B_0$-dependency of a measured magnetic resonance (MR) signal.

17. The method according to claim 1, wherein the predetermined threshold value is based on a spin dephasing at the time of the main lobe.

18. A magnetic resonance imaging (MRI) device, comprising:
   an electromagnetic subsystem configured to image a subject; and
   a controller configured to control the electromagnetic subsystem to:
      perform a spoiled gradient echo sequence with a $B_0$ magnetic field strength of at most 1.5 T;
      apply, as part of the spoiled gradient echo sequence, a slice select gradient acting as a spoil gradient; and
      apply a predetermined radio frequency (RF) pulse in the spoiled gradient echo sequence simultaneously with the slice select gradient, wherein a time-bandwidth product (TBP) of the RF pulse is set so that: a majority of an energy of the RF pulse is transmitted in its central main lobe, and a provided predetermined threshold value is met through a stepwise increase from a given starting value.

* * * * *